(12) United States Patent
Hossain et al.

(10) Patent No.: US 12,214,062 B1
(45) Date of Patent: Feb. 4, 2025

(54) ORGANIC DENTAL CROWN AND METHOD OF FABRICATING THE DENTAL CROWN

(71) Applicant: IMAM MOHAMMAD IBN SAUD ISLAMIC UNIVERSITY, Riyadh (SA)

(72) Inventors: Abm Sharif Hossain, Riyadh (SA); Hassan Ahmed Rudayni, Riyadh (SA); Mohammad Saad Aleissa, Riyadh (SA); Mohammed Musa Zahrany, Riyadh (SA); Abdulrahman Alhudhaibi, Riyadh (SA); Fazliny Abdul Rahman, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 18/793,272

(22) Filed: Aug. 2, 2024

(51) Int. Cl.
| | |
|---|---|
| A61K 6/898 | (2020.01) |
| A61C 5/73 | (2017.01) |
| A61C 5/77 | (2017.01) |
| A61C 13/08 | (2006.01) |
| A61K 6/17 | (2020.01) |
| A61K 6/80 | (2020.01) |
| A61K 6/831 | (2020.01) |
| A61K 6/887 | (2020.01) |

(52) U.S. Cl.
CPC ............. *A61K 6/898* (2020.01); *A61C 5/73* (2017.02); *A61C 5/77* (2017.02); *A61C 13/081* (2013.01); *A61K 6/17* (2020.01); *A61K 6/80* (2020.01); *A61K 6/831* (2020.01); *A61K 6/887* (2020.01)

(58) Field of Classification Search
CPC ........ A61K 6/898; A61K 6/887; A61K 6/831; A61K 6/80; A61K 6/17; A61C 5/77; A61C 5/73; A61C 13/081
See application file for complete search history.

(56) References Cited

U.S. PATENT DOCUMENTS

| | | | |
|---|---|---|---|
| 7,812,065 B2 * | 10/2010 | Bublewitz | A61K 6/90 264/16 |
| 2024/0043341 A1 * | 2/2024 | Bär | C04B 35/6264 |

FOREIGN PATENT DOCUMENTS

| | | |
|---|---|---|
| CN | 107163527 B | 1/2019 |
| CN | 117205360 A | 12/2023 |
| GB | 2461475 B | 9/2010 |

OTHER PUBLICATIONS

Ali Mohammed Korsheed et al., "Preparation and Characterization of Natural Fish Bone as an Implant Material", Journal of Medicinal and Chemical Sciences, vol. 6, Issue 3, Mar. 2023, pp. 688-678.

* cited by examiner

*Primary Examiner* — Ralph A Lewis
(74) *Attorney, Agent, or Firm* — Oblon, McClelland, Maier & Neustadt, L.L.P.

(57) ABSTRACT

An organic nanocomposite dental crown includes an organic composition, a starch biopolymer, and at least one organic polymer-forming agent. The starch biopolymer includes date seed-based nanostarch, coconut shell-based nanostarch, fish bone, and camel bone powder. The organic composition includes one of fruit waste, placenta glue, seed-based gel, natural glue, glycerin, and organic dye. The nanostarch biocomposite includes particles with an average particle size of less than 25 nm, dispersed in a solid matrix. The dental crown has a molded structure with a height of 10 mm or less and a width of 9.5 mm or less.

20 Claims, 5 Drawing Sheets

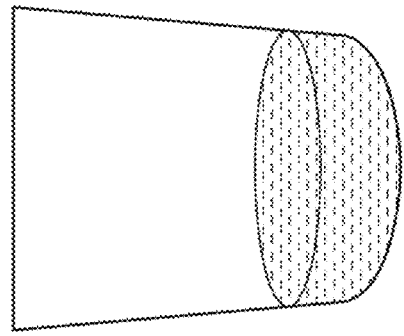
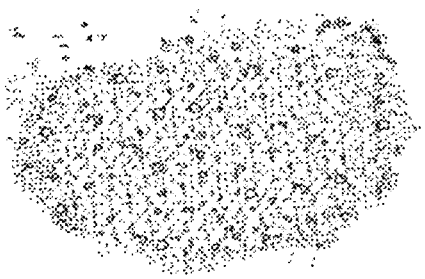
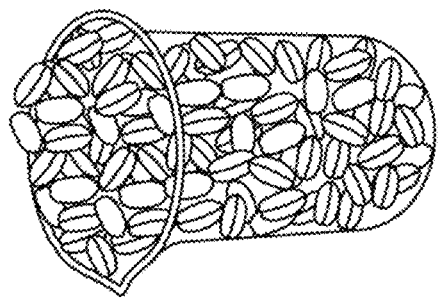
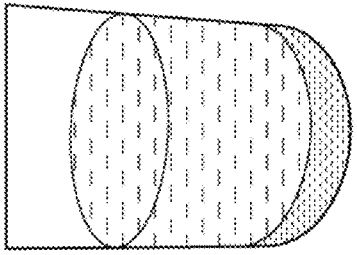
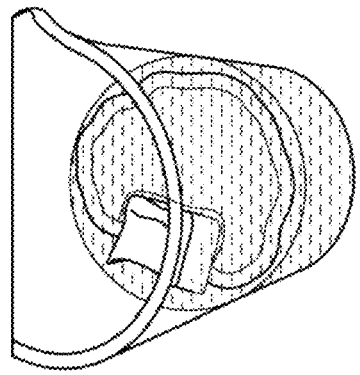
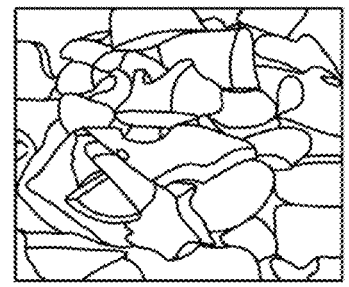
FIG. 2A  FIG. 2B  FIG. 2C  FIG. 2D  FIG. 2E  FIG. 2F

ORGANIC DENTAL CROWN AND METHOD OF FABRICATING THE DENTAL CROWN

BACKGROUND

Technical Field

The present disclosure is directed to a dental crown, more particularly, directed to a dental crown formed of organically derived from biocomposites, and also a method of fabricating the dental crown.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

A dental crown is a tooth-shaped "cap" that is placed over a tooth to cover the tooth to restore its shape and size, strength, and improve its appearance. Crowns, when cemented into place, fully encase the entire visible portion of a tooth that lies at and above the gum line. Crowns are made from a variety of materials, including metal crowns, ceramic (porcelain) crowns, and composite resin crowns. The type of material used may depend on the tooth being treated.

Metallic crowns are generally made up of gold, platinum, and base-metal alloys. These crowns are very effective in that they require minimal tooth preparation (as only a thin layer of the enamel must be removed to fit the crown) and are known for their durability. These crowns, however, can be quite expensive and have a metallic color, making the metallic crown obvious among the surrounding teeth.

Porcelain fused to metal (PFM) crowns are a suitable alternative to metal crowns. These crowns look natural because the crown's shade can be matched to the natural teeth. Porcelain crowns are also very durable. Despite these benefits, PFM crowns have several disadvantages such as increased cost. Further, the presence of a metal component means a dark line usually appears in the area where the crown meets the tooth, which can decrease the aesthetic value of the crown. There is also a possibility that the porcelain portion of the PFM crown may chip off over time, causing the adjacent teeth to wear down.

Ceramic (porcelain) crowns are another alternative for dental crowns. They can be matched to natural tooth color, making them an aesthetically pleasing option. These crowns, however, are not as durable as metal crowns and may also weaken the permanent tooth adjacent to them. To make a ceramic crown stronger and thicker, more of the original tooth may need to be removed, which may be undesirable.

Composite resin crowns are another type of dental crown that may be a suitable alternative for people allergic to metal and ceramic materials. Composite resin may insulate the tooth and reduce sensitivity. However, because they are not as durable as metal or ceramic crowns, composite resins can be susceptible to chipping. Composite resin crowns can, however, be easily repaired by adding more composite to the damaged area, rather than having to replace the entire crown. Compared to other types of crowns, such as metal or ceramic, composite resin crowns are more likely to wear down or fracture over time. This is especially true for people who grind their teeth or use their teeth for activities other than eating. Further, composite resin crowns are more prone to staining than other materials, which could affect their appearance over time.

Despite the availability of several types of dental crown materials, there is a need for one that has increased durability, increase aesthetics, and lower cost. Therefore, one objective of this disclosure is to develop a cost-effective nanocomposite material, developed from biological sources, for medical and dental use. A further objective of this disclosure is to provide a dental crown material that is biodegradable, organic, biologically inert, and offers superior mechanical strength without impacting the environment.

SUMMARY

In an exemplary embodiment, an organic dental crown is disclosed. The organic dental crown comprises a nanostarch biocomposite comprising an organic composition and a starch biopolymer; and at least one organic polymer-forming agent. The starch biopolymer comprises date seed-based nanostarch, coconut shell-based nanostarch, fish bone, and camel bone powder. The organic composition comprises at least one of a fruit waste, a placenta glue, a seed-based gel, a natural glue, a glycerin, and an organic dye. The nanostarch biocomposite comprises particles having an average particle size of less than 25 nanometer (nm) dispersed in a solid matrix. The dental crown has a molded structure having a height of 10 millimeter (mm) or less and a width of 9.5 mm or less.

In some embodiments, the particles of the nanostarch biocomposite have an average particle size of 15 nm or less.

In some embodiments, the organic polymer-forming agent is at least one selected from the group consisting of a plasticizer, an adhesive, a starch, and a glycolic acid copolymer.

In some embodiments, the organic polymer-forming agent comprises polyvinyl chloride.

In some embodiments, the molded structure has an outer layer and a base layer, wherein the base layer and the outer layer have a thickness of 1 mm or less.

In some embodiments, the dental crown has a tensile strength of 80 to 120 mPa/kg·m$^3$.

In some embodiments, the organic dye is at least one selected from the group consisting of a mangosteen peel dye and a pomegranate peel dye.

In some embodiments, the dental crown has a lightness (L*) of 70 to 90.

In some embodiments, the dental crown has a chroma (C) value of 15 to 30.

In some embodiments, the dental crown has a tensile modulus of 1.5 to 2.5 GPa.

In some embodiments, the dental crown has a hue (H) of 85 to 100.

In some embodiments, the dental crown has an a* value of −2 to 0.50.

In some embodiments, the dental crown has a b* value of 15 to 30.

In another exemplary embodiment, a method of fabricating the dental crown is disclosed. The method comprises hydrolyzing a mixture of a starch biopolymer and an organic composition with at least one inorganic acid to obtain a nanostarch biocomposite, combining at least one organic polymer-forming agent with the nanostarch biocomposite to form a dental mixture, then pressing the dental mixture into a molded structure, and hardening or curing the molded structure to form the dental crown.

In some embodiments, the inorganic acid is selected from the group consisting of hydrochloric acid, nitric acid, hydrobromic acid, sulfuric acid, hydrofluoric acid, and phosphorous acid.

In some embodiments, the inorganic acid is sulfuric acid and nitric acid.

In some embodiments, the method comprises pyrolyzing a mixture of date seed-based nanostarch, coconut shell-based nanostarch, fish bone, and camel bone powder in an oven at a temperature of 120 to 160° C. for 3 to 8 hours (h).

In some embodiments, the method of curing is photocuring or thermal curing.

In some embodiments, the molded structure is cured with a light curing device for 10 to 30 seconds at a light intensity of 250 to 850 mW/cm$^2$.

In some embodiments, the molded structure is cured at a temperature of 100 to 160° C. for 3 to 6 h.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 2A is a pictorial image of a waste date seed, according to certain embodiments.

FIG. 2B is a pictorial image of the waste date seed ground into a powder, according to certain embodiments.

FIG. 2C is a pictorial image showing acid hydrolysis of the powder of the waste date seed, according to certain embodiments.

FIG. 2D is a pictorial image of a camel bone, and a solution obtained on acid hydrolysis of the camel bone, according to certain embodiments.

FIG. 2E is a pictorial image of the solution obtained from the camel bone after washing, according to certain embodiments.

FIG. 2F is a pictorial image of a coconut shell, according to certain embodiments. nanoparticles obtained from the coconut shell, according to certain embodiments.

DETAILED DESCRIPTION

Figure 1:
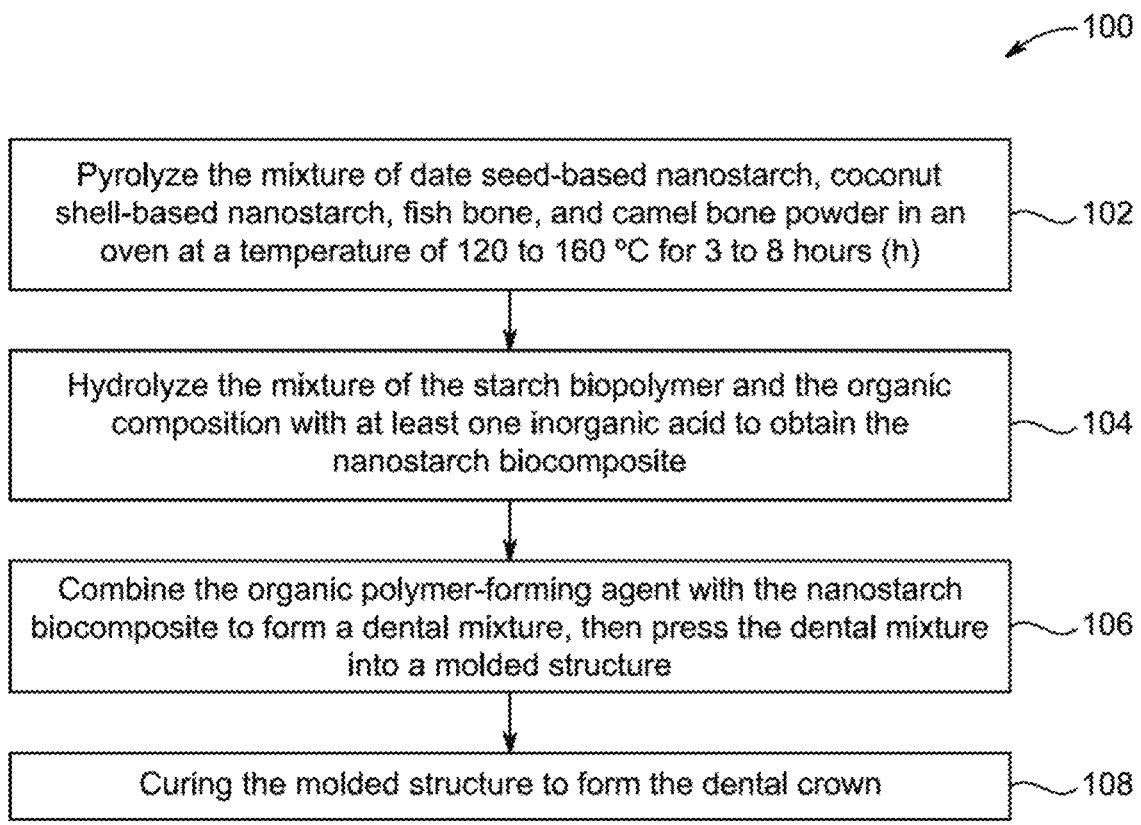
FIG. 1 is a flowchart depicting a method of preparation of an organic dental crown, according to certain embodiments.

In the drawings, like reference numerals designate identical or corresponding parts throughout the several views. Further, as used herein, the words "a", "an" and the like generally carry a meaning of "one or more", unless stated otherwise.

Furthermore, the terms "approximately," "approximate", "about" and similar terms generally refer to ranges that include the identified value within a margin of 20%, 10%, or preferably 5%, and any values therebetween.

As used herein, "particle size" and "pore size" may be considered the lengths or longest dimensions of a particle and a pore opening, respectively.

As used herein, the term "organic" refers to a substance or material that can be produced from naturally occurring substances or materials.

As used herein, the term "polymer" refers to a large molecule comprising a chain of smaller repeating units of monomers.

As used herein, the term "plasticizer" refers to substances added to a polymeric material to improve the plasticity and flexibility of the polymer.

As used herein, the term "curing" refers to a chemical process employed in polymer chemistry and process engineering that produces the toughening or hardening of a polymer material by cross-linking of polymer chains. Curing can be induced by various stimuli such as heat, light, radiation, electron beams, or chemical additives.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100 wt. %.

Aspects of the present disclosure are directed to biodegradable (organic) dental crown formed from readily available organic sources, including date seed and coconut shell-based nano-starch and fish bone, a seashell (oyster shell), and camel bone powder. The subject matter discussed herein involves using biodegradable materials, and the dental crowns prepared from these materials offer several advantages over traditional synthetic crowns made from metal, ceramic, and plastics which are not toxic, biodegradable, and cost-effective.

According to the first aspect of the present disclosure, an organic dental crown is described. The organic dental crown comprises a nanostarch biocomposite. The nanostarch biocomposite comprises a starch biopolymer and an organic composition. The starch biocomposite is obtained from a biobased material. The biobased materials include naturally occurring, renewable sources and may be of plant or animal origin. In certain embodiments, the starch source is a plant-based source. In a specific embodiment, the starch source is an animal source. In yet another embodiment, the starch source comprises plants and animal sources. The starch biocomposite of the present disclosure is obtained from date seed, coconut shell, oyster, fish bone, and camel bone powder, which contain a large amount of starch.

In an embodiment, the starch biocomposite comprises nanoparticles derived from date seed. In certain embodiments, the starch biocomposite comprises nanoparticles derived from the knee bone of an animal, preferably a camel. The camel knee bone is crushed to form a powder, and the powder particles are converted to nanoparticles by acid hydrolysis. In an embodiment, the starch biocomposite comprises nanoparticles derived from coconut shells. The coconut shell is crushed to form a powder, and the powder is converted to nanoparticles by acid hydrolysis. In some embodiments, the starch biocomposite comprises nanoparticles derived from oyster shells and fish bone. The oyster shells and fish bones are crushed to form a powder, and the powder particles are converted to nanoparticles by acid hydrolysis.

The organic composition comprises a mixture of organic substances in an amount of about 40 to about 50 wt. %, preferably 44 to 45 wt. % of the total weight of the nanostarch biocomposite. The organic substances include one or more of fruit waste, placenta glue, seed-based gel, natural glue, glycerin, and organic dye. The placenta glue is obtained from the placenta of an elephant apple (Dillenia indica). In some embodiments, the organic composition comprises placenta glue from Dillenia indica at about 1 to 10 wt. %, preferably 2 to 9 wt. %, preferably 3 to 8 wt. %, preferably 4 to 7 wt. %, preferably 5 to 6 wt. %, and more preferably about 5 wt. %. The seed-based gel is obtained from fenugreek (*Trigonella* foenum). In some embodiments, the organic composition comprises *Trigonella* foenum of about 1 to 10 wt. %, preferably 2 to 9 wt. %, preferably 3 to 8 wt. %, preferably 4 to 7 wt. %, preferably 5 to 6 wt. %, and more preferably about 5 wt. %. Natural glue and gels are particularly useful as they contain high amounts of polysaccharides and are water soluble and biodegradable. In some embodiments, the organic composition comprises fresh gum from Lannea sp. in about 1 to 10 wt. %, preferably 2 to 9 wt. %, preferably 3 to 8 wt. %, preferably 4 to 7 wt. %, preferably 5 to 6 wt. %, and more preferably about 5 wt. %; and gum obtained from plant Acacia nilotica in an amount of about 1 to 10 wt. %, preferably 2 to 9 wt. %, preferably 3 to 8 wt. %, preferably 4 to 7 wt. %, preferably 5 to 6 wt. %, and more preferably about 5 wt. %. Glycerin can be obtained from animal fat. In an embodiment, it is obtained from chicken fat, particularly from chicken gut/skin oil. Glycerin is highly soluble in water and enhances the degradability of a polymer when added as a plasticizing agent. In some embodiments, the organic composition comprises chicken gut/skin oil as the glycerin source in an amount of about 5 to 15 wt. %, preferably 6 to 12 wt. %, preferably 8 to 10 wt. %, preferably 8 wt. %.

In some embodiments, the organic dye is obtained from fruit peels of pomegranate and/or mangosteen. Mangosteen fruit peels, known for their juicy, sweet, and sour taste and high fiber content from tropical trees, are added to impart a desired color to the organic composition. These peels are valued for their medicinal properties, including antimicrobial, anti-inflammatory, and anti-parasitic functions. Similarly, pomegranate peels are added to provide the desired color to the organic composition. Pomegranate peel contains bioactive compounds, including tannins, starch, cellulose, lignins, and pectins. In some embodiments, the organic composition comprises the organic dye obtained from pomegranate peels, where the dye is present in an amount preferably about 5 to 15 wt. %, preferably 6 to 12 wt. %, preferably 8 to 10 wt. %, preferably 8 wt. %. In some embodiments, the organic composition comprises the organic dye obtained from mangosteen peels, where the dye is present in an amount preferably about 5 to 15 wt. %, preferably 6 to 12 wt. %, preferably 8 to 10 wt. %, preferably 8 wt. %.

In some embodiments, the nanostarch biocomposite comprises particles having an average particle size of less than 25 nm, preferably less than 24 nm, preferably less than 23 nm, preferably less than 22 nm, preferably less than 21 nm, preferably less than 20 nm, preferably less than 19 nm, preferably less than 18 nm, preferably less than 17 nm, preferably less than 16 nm, and most preferably less than 15 nm.

In one embodiment, the organic dental crown further comprises one or more organic polymer-forming agent(s). The organic polymer-forming agents help control the polymerization process and, when incorporated into the organic dental crown, provide a desirable amount of mechanical strength, plasticity, and flexibility. The organic polymer-forming agents may allow the organic dental crown to be shaped into a rectangular, a cylindrical, or a spherical form. In one embodiment, the organic polymer-forming agent(s) form a solid matrix into which the nanostarch biocomposite is dispersed.

In an embodiment, the organic polymer-forming agent is at least one of a plasticizer, an adhesive, a starch, and a glycolic acid copolymer. In one embodiment, the organic polymer-forming agent may be a plasticizer, such as a polyvinyl chloride (PVC), a polylactic acid, a polyglycolic acid, and a polylactic glycolic acid (PLGA). Organic polymers and organic polymer blends may be used as plasticizers to impart the desired strength, flexibility, and shape to the nanostarch biocomposite. In one embodiment, the organic polymer-forming agent in the nanocomposite comprises a polyvinyl chloride. In a preferred embodiment, the nanocomposite comprises a polyvinyl chloride in an amount of about 5 to 30 wt. %, preferably 6 to 29 wt. %, preferably 7 to 28 wt. %, preferably 8 to 27 wt. %, preferably 9 to 26 wt. %, preferably 10 to 25 wt. %, preferably 10 to 24 wt. %, preferably 10 to 23 wt. %, preferably 10 to 22 wt. %, preferably 10 to 21 wt. %, preferably 10 to 20 wt. %, preferably 10 to 19 wt. %, preferably 10 to 18 wt. %, preferably 10 to 17 wt. %, preferably 10 to 16 wt. %, preferably 10 to 15 wt. %, preferably 10 to 14 wt. %, preferably 10 to 13 wt. %, preferably 10 to 12 wt. %, preferably 10 to 11 wt. %, most preferably 10 wt. %.

In some embodiments, the organic-polymer-forming agent further comprises an adhesive, which aid in bonding the components of the dental crown. In an embodiment, the adhesive is a polymeric resin such as an acrylic polymer. In some embodiments, the acrylate adhesive may be a cyanoacrylate adhesive, a methyl methacrylate, or a derivative thereof. In a preferred embodiment, the acrylate adhesive is a cyanoacrylate adhesive. In some embodiments, the adhesive is present in amount of 1 to 10 wt. %, preferably 2 to 9 wt. %, preferably 3 to 8 wt. %, preferably 4 to 7 wt. %, preferably 5 to 6 wt. %, and most preferably about 5 wt. %. In one embodiment, the organic-polymer-forming agents may further comprise a starch. Starch may be obtained from renewable biobased materials such as date seeds, coconut shell, oyster, fish bone, camel bone powder, mangosteen fruit peels, and pomegranate fruit peels. In some embodiments, starch obtained from corn, potato, tapioca, and wheat may also be used. In an embodiment, starch is present in about 5 to 15 wt. %, preferably 6 to 14 wt. %, preferably 7 to 13 wt. %, preferably 8 to 12 wt. %, preferably 8 to 11 wt. %, preferably 8 to 10 wt. %, preferably 8 to 19 wt. %, and most preferably 8 wt. %. In some embodiments, the organic-polymer-forming agent may further comprise a glycolic acid copolymer. In a preferred embodiment, the glycolic acid copolymer is a PLGA. In this embodiment, the PLGA is present in an amount of 1 to 10 wt. %, preferably 2 to 9 wt. %, preferably 3 to 8 wt. %, preferably 4 to 7 wt. %, preferably 5 to 6 wt. %, and more preferably about 5 wt. %.

In certain embodiments, a total amount of polyvinyl chloride, polylactic glycolic acid, acrylate adhesive, and starch in the organic dental crown is about 20 to 30 wt. %. In a preferred embodiment, the organic polymer-forming agents include about 5 to 15 wt. % PVC, 1 to 10 wt. % acrylate adhesive, 1 to 10 wt. % PLGA, and 1 to 15 wt. % starch, preferably 6 to 14 wt. % PVC, 2 to 9 wt. % acrylate adhesive, 2 to 9 wt. % PLGA, and 2 to 14 wt. % starch, preferably 7 to 13 wt. % PVC, 3 to 8 wt. % acrylate adhesive, 3 to 8 wt. % PLGA, and 3 to 13 wt. % starch, preferably 8 to 12 wt. % PVC, 4 to 7 wt. % acrylate adhesive, 4 to 7 wt. % PLGA, and 4 to 12 wt. % starch, preferably 9 to 11 wt. % PVC, 5 to 6 wt. % acrylate adhesive, 5 to 6 wt. % PLGA, and 5 to 11 wt. % starch, preferably 9 to 11 wt. % PVC, 5 to 6 wt. % acrylate adhesive, 5 to 6 wt. % PLGA, and 6 to 10 wt. % starch, preferably 9 to 11 wt. % PVC, 5 to 6 wt. % acrylate adhesive, 5 to 6 wt. % PLGA, and 7 to 9 wt. % starch, most preferably 10 wt. % PVC, 5 wt. % acrylate adhesive, 5 wt. % PLGA, and 8 wt. % starch.

The dental crown has a molded structure with a height of 10 mm or less and a width of 9.5 mm or less. The molded structure has an outer layer and a base layer, where the base layer and the outer layer have a thickness of less than 1 mm.

Referring to FIG. 1, a method of fabricating the dental crown is disclosed. The order in which the method described is not intended to be construed as a limitation, and any number of the described method steps can be combined in any order to implement the method for nanocomposite organic teeth manufacturing. Additionally, individual steps may be removed or skipped from the method without departing from the spirit and scope of the present disclosure.

At step 102, the method 100 comprises pyrolyzing a mixture of date seed-based nanostarch, coconut shell-based nanostarch, fish bone, and camel bone powder in an oven at 120 to 160° C. for 3 to 8 hours (h). The mixture is decomposed in an inert environment at temperatures of about 120° C. to about 140° C. In some embodiments, the pomegranate peels are heated at temperatures of about 121° C., preferably about 122° C., preferably about 123° C., preferably about 124° C., preferably about 125° C., preferably about 126° C., preferably about 127° C., preferably about 128° C., preferably about 129° C., preferably about 130° C., preferably about 131° C., preferably about 132° C., preferably about 133° C., preferably about 134° C., preferably about 135° C., preferably about 136° C., preferably about 137° C., preferably about 138° C., preferably about 139° C., most preferably about 140° C. The heating may be performed in any suitable equipment, such as a reactor, including a rotary kiln reactor, a fluidized bed reactor, a pyrolysis reactor, a microwave pyrolysis reactor, or an oven. In a preferred embodiment, the pomegranate peels are heated in an oven at 140° C. for about 3 to 4 hours, preferably for about 4 hours.

At step 104, the method 100 comprises hydrolyzing a mixture of the starch biopolymer and the organic composition with at least one inorganic acid to obtain the nanostarch biocomposite. The pyrolyzed mixture, as obtained in step 102, is subjected to hydrolysis by an acid. In one embodiment, the acid may be organic or inorganic. In a preferred embodiment, the acid is an inorganic acid. The inorganic acid is at least one selected from hydrochloric acid, nitric acid, hydrobromic acid, sulfuric acid, hydrofluoric acid, and phosphorous acid. In one embodiment, the inorganic acid is sulfuric acid. In another embodiment, the inorganic acid is nitric acid. In a another embodiment, the inorganic acid is sulfuric and nitric acid. In one embodiment, the pyrolyzed date seeds are hydrolyzed by nitric acid. In this embodiment, the concentration of nitric acid may be about 80 to 90%. In some embodiments, nitric acid concentrations are about 81%, about 82%, about 83%, about 84%, about 85%, about 86%, about 87%, about 88%, about 89%, or about 90%. In a preferred embodiment, nitric acid concentration may be about 85%. In one embodiment, the pyrolyzed fish bone, seashell, and camel bone are hydrolyzed by sulfuric acid. The concentration of sulfuric acid is about 80 to 90%. In some embodiments, sulfuric acid concentrations are about 81%, 82%, 83%, 84%, 85%, 86%, 87%, 88%, 89%, or 90%. In a preferred embodiment, sulfuric acid concentration may be about 90%. In one embodiment, the pyrolyzed fish bone, seashell, and camel bone are hydrolyzed by sulfuric acid and nitric acid. The concentration of nitric acid and sulfuric acid is about 80 to 90%. In one embodiment, the nitric acid and sulfuric acid may be in a ratio of 1:1 to 5:1 nitric acid to sulfuric acid, preferably 1:1 to 4:1 nitric acid to sulfuric acid, preferably 1:1 to 3:1 nitric acid to sulfuric acid, most preferably 1:1 to 2:1 nitric acid to sulfuric acid.

In an embodiment, each component of the starch biopolymer is hydrolyzed individually to obtain their respective nanoparticles before mixing the starch biopolymer with the organic composition. In one embodiment, the date seeds are preferably waste date seeds (FIG. 2A). In another embodiment, the date seeds are ground in a date seed grinder or a mill machine to a powder form (FIG. 2B). The date seeds are ground until a particle size of about 1 to 100 mm is achieved. In some embodiments, the particle size of date seeds is about 5 to 95 mm, preferably about 10 to 90 mm, preferably about 15 to 85 mm, preferably about 20 to 80 mm, preferably about 25 to 85 mm, preferably about 30 to 80 mm, preferably about 35 to 75 mm, preferably about 40 to 70 mm, preferably about 45 to 65 mm, preferably about 50 to 60 mm, most preferably about 50 mm. The date seed powder is further hydrolyzed using an acid. In one embodiment, the pyrolyzed date seed powder is hydrolyzed by nitric acid. In another embodiment, the pyrolyzed date seed powder is hydrolyzed by sulfuric acid. In yet another embodiment, the pyrolyzed date seed powder is hydrolyzed by nitric acid and sulfuric acid. The concentration of nitric acid may be about 80 to 90%. In one embodiment, nitric acid concentrations are about 81%, 82%, 83%, 84%, 85%, 86%, 87%, 88%, 89%, or 90%. In another embodiment, nitric acid concentration may be about 85% (FIG. 2C). In one embodiment, the concentration of sulfuric acid is about 80 to 90%. In some embodiments, sulfuric acid concentrations are about 81%, 82%, 83%, 84%, 85%, 86%, 87%, 88%, 89%, or 90%. In one embodiment, sulfuric acid concentration may be about 90%. In one embodiment, the nitric acid and sulfuric acid may be in a ratio of 1:1 to 5:1 nitric acid to sulfuric acid, preferably 1:1 to 4:1 nitric acid to sulfuric acid, preferably 1:1 to 3:1 nitric acid to sulfuric acid, most preferably 1:1 to 2:1 nitric acid to sulfuric acid.

In some embodiments, the method comprises grinding the camel knee bone (FIG. 2D) to a powder form. The grinding of camel knee bone can be performed in a bone grinder or milling machine. The camel knee bone is ground until a particle size of about 1 to 100 mm is achieved. In some embodiments, the particle size of the camel knee bone is about 5 to 95 mm, preferably about 10 to 90 mm, preferably about 15 to 85 mm, preferably about 20 to 80 mm, preferably about 25 to 85 mm, preferably about 30 to 80 mm, preferably about 35 to 75 mm, preferably about 40 to 70 mm, preferably about 45 to 65 mm, preferably about 50 to 60 mm, most preferably about 50 mm. The camel knee bone powder is further hydrolyzed using an acid to obtain nanoparticles. The acid is an inorganic acid. The inorganic acid is one selected from hydrochloric acid, nitric acid, hydrobromic acid, sulfuric acid, hydrofluoric acid, and phosphorous acid. In one embodiment, the pyrolyzed camel knee bone powder is hydrolyzed by nitric acid. In another embodiment, the pyrolyzed camel knee bone powder is hydrolyzed by sulfuric acid. In yet another embodiment, the pyrolyzed camel knee bone powder is hydrolyzed by nitric acid and sulfuric acid. The concentration of nitric acid may be about 80 to 90%. In one embodiment, nitric acid concentrations are about 81%, 82%, 83%, 84%, 85%, 86%, 87%, 88%, 89%, or 90%. In another embodiment, nitric acid concentration may be about 85%. In one embodiment, the concentration of sulfuric acid is about 80 to 90%. In some embodiments, sulfuric acid concentrations are about 81%, 82%, 83%, 84%, 85%, 86%, 87%, 88%, 89%, or 90%. In one embodiment, sulfuric acid concentration may be about 90%. The concentration of nitric acid and sulfuric acid is about 80 to 90%. In one embodiment, the nitric acid and sulfuric acid may be in a ratio of 1:1 to 5:1 nitric acid to sulfuric acid, preferably 1:1 to 4:1 nitric acid to sulfuric acid, preferably 1:1 to 3:1 nitric acid to sulfuric acid, most preferably 1:1 to 2:1 nitric acid to sulfuric acid. After acid hydrolysis, the camel knee bone is washed with a solvent, preferably water (FIG. 2E).

Figure 2G:
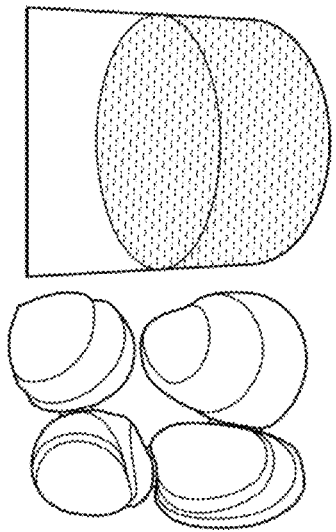
FIG. 2G is a pictorial image of a solution obtained on acid hydrolysis of the coconut shell, according to certain embodiments.

In some embodiments, the method comprises grinding the coconut shell (FIG. 2F) to a powder form. The grinding of coconut shells can be performed in a milling machine. The coconut shell is ground until a particle size of about 1 to 100 mm is achieved. In some embodiments, the particle size of the coconut shell is about 5 to 95 mm, preferably about 10 to 90 mm, preferably about 15 to 85 mm, preferably about 20 to 80 mm, preferably about 25 to 85 mm, preferably about 30 to 80 mm, preferably about 35 to 75 mm, preferably about 40 to 70 mm, preferably about 45 to 65 mm, preferably about 50 to 60 mm, most preferably about 50 mm. The coconut shell powder is further hydrolyzed using an acid to obtain nanoparticles. The acid is an inorganic acid. The inorganic acid is one selected from hydrochloric acid, nitric acid, hydrobromic acid, sulfuric acid, hydrofluoric acid, and phosphorous acid. In one embodiment, the pyrolyzed coconut shell powder is hydrolyzed by nitric acid. In another embodiment, the pyrolyzed coconut shell powder is hydrolyzed by sulfuric acid. In yet another embodiment, the pyrolyzed coconut shell powder is hydrolyzed by nitric acid and sulfuric acid. The concentration of nitric acid may be about 80 to 90%. In one embodiment, nitric acid concentrations are about 81%, 82%, 83%, 84%, 85%, 86%, 87%, 88%, 89%, or 90%. In another embodiment, nitric acid concentration may be about 85%. In one embodiment, the concentration of sulfuric acid is about 80 to 90%. In some embodiments, sulfuric acid concentrations are about 81%, 82%, 83%, 84%, 85%, 86%, 87%, 88%, 89%, or 90%. In one embodiment, sulfuric acid concentration may be about 90%. In one embodiment, the nitric acid and sulfuric acid may be in a ratio of 1:1 to 5:1 nitric acid to sulfuric acid, preferably 1:1 to 4:1 nitric acid to sulfuric acid, preferably 1:1 to 3:1 nitric acid to sulfuric acid, most preferably 1:1 to 2:1 nitric acid to sulfuric acid. After acid hydrolysis, the coconut shell powder is washed with a solvent, preferably water (FIG. 2G).

In some embodiments, the method comprises preparing nanoparticles from fish bone/scales. An inorganic acid is used to hydrolyze the fish bone/scales. The acid is an inorganic acid selected from hydrochloric acid, nitric acid, hydrobromic acid, sulfuric acid, hydrofluoric acid, and phosphorous acid. In one embodiment, the pyrolyzed fish bone/scales are hydrolyzed by nitric acid. In another embodiment, the pyrolyzed fish bone/scales are hydrolyzed by sulfuric acid. In yet another embodiment, the pyrolyzed fish bone/scales are hydrolyzed by nitric acid and sulfuric acid. The concentration of nitric acid may be about 80 to 90%. In one embodiment, nitric acid concentrations are about 81%, 82%, 83%, 84%, 85%, 86%, 87%, 88%, 89%, or 90%. In another embodiment, nitric acid concentration may be about 85%. In one embodiment, the concentration of sulfuric acid is about 80 to 90%. In some embodiments, sulfuric acid concentrations are about 81%, 82%, 83%, 84%, 85%, 86%, 87%, 88%, 89%, or 90%. In one embodiment, sulfuric acid concentration may be about 90%. In one embodiment, the nitric acid and sulfuric acid may be in a ratio of 1:1 to 5:1 nitric acid to sulfuric acid, preferably 1:1 to 4:1 nitric acid to sulfuric acid, preferably 1:1 to 3:1 nitric acid to sulfuric acid, most preferably 1:1 to 2:1 nitric acid to sulfuric acid (FIG. 2H).

Figure 2I:
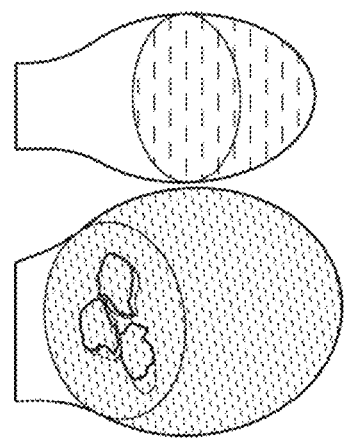
FIG. 2I is a pictorial image of seashells (oyster), and a solution obtained on acid hydrolysis of the seashells, according to certain embodiments.
Figure 2H:
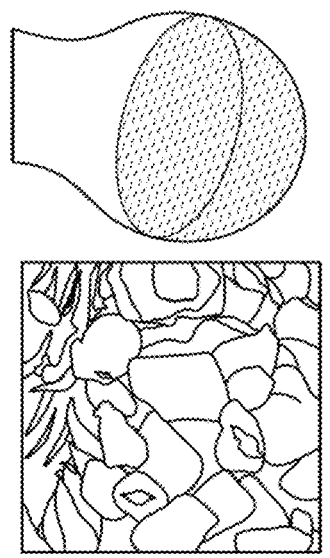
FIG. 2H is a pictorial image of fish scales, and a solution obtained on acid hydrolysis of the fish scales, according to certain embodiments.

In some embodiments, the method comprises preparing nanoparticles from seashells (oysters) (FIG. 2I). An inorganic acid hydrolyzes the seashells to obtain nanoparticles. The acid is an inorganic acid selected from hydrochloric acid, nitric acid, hydrobromic acid, sulfuric acid, hydrofluoric acid, and phosphorous acid. In one embodiment, the pyrolyzed seashells are hydrolyzed by nitric acid. In another embodiment, the pyrolyzed seashells are hydrolyzed by sulfuric acid. In yet another embodiment, the pyrolyzed seashells are hydrolyzed by nitric acid and sulfuric acid. The concentration of nitric acid may be about 80 to 90%. In one embodiment, nitric acid concentrations are about 81%, 82%, 83%, 84%, 85%, 86%, 87%, 88%, 89%, or 90%. In another embodiment, nitric acid concentration may be about 85%. In one embodiment, the concentration of sulfuric acid is about 80 to 90%. In some embodiments, sulfuric acid concentrations are about 81%, 82%, 83%, 84%, 85%, 86%, 87%, 88%, 89%, or 90%. In one embodiment, sulfuric acid concentration may be about 90%. In one embodiment, the nitric acid and sulfuric acid may be in a ratio of 1:1 to 5:1 nitric acid to sulfuric acid, preferably 1:1 to 4:1 nitric acid to sulfuric acid, preferably 1:1 to 3:1 nitric acid to sulfuric acid, most preferably 1:1 to 2:1 nitric acid to sulfuric acid.

The organic composition is then added to the hydrolyzed mixture. The organic composition comprises a mixture of organic substances selected from one or more of fruit waste, placenta glue, seed-based gel, natural glue, glycerin, and organic dye. In one embodiment, Waste elephant apple (Dillenia indica) placenta glue, fenugreek (*Trigonella* foenum) gel, natural glue [fresh gum (Lannea sp)], Acacia nilotica gum, chicken skin oil-based glycerin, mangosteen peel dye, and pomegranate peel dye comprises the organic composition added to the hydrolyzed mixture to form the nanostarch biocomposite. In one embodiment, the Waste elephant apple placenta glue is present in an amount of 1 to 10 wt. %, preferably 2 to 9 wt. %, preferably 3 to 8 wt. %, preferably 4 to 7 wt. %, preferably 5 to 6 wt. %, most preferably 5 wt. %. In one embodiment, the fenugreek gel is present in an amount of 1 to 10 wt. %, preferably 2 to 9 wt. %, preferably 3 to 8 wt. %, preferably 4 to 7 wt. %, preferably 5 to 6 wt. %, most preferably 5 wt. %. In one embodiment, the natural glue is present in an amount of 1 to 10 wt. %, preferably 2 to 9 wt. %, preferably 3 to 8 wt. %, preferably 4 to 7 wt. %, preferably 5 to 6 wt. %, most preferably 5 wt. %. In one embodiment, the Acacia nilotica gum is present in an amount of 1 to 10 wt. %, preferably 2 to 9 wt. %, preferably 3 to 8 wt. %, preferably 4 to 7 wt. %, preferably 5 to 6 wt. %, most preferably 5 wt. %. In one embodiment, the chicken skin oil-based glycerin is present in an amount of 5 to 15 wt. %, preferably 6 to 14 wt. %, preferably 7 to 13 wt. %, preferably 8 to 12 wt. %, preferably 8 to 11 wt. %, preferably 8 to 10 wt. %, preferably 8 to 9 wt. %, most preferably 8 wt. %. In one embodiment, the mangosteen peel dye is present in an amount of 5 to 15 wt. %, preferably 6 to 14 wt. %, preferably 7 to 13 wt. %, preferably 8 to 12 wt. %, preferably 8 to 11 wt. %, preferably 8 to 10 wt. %, preferably 8 to 9 wt. %, most preferably 8 wt. %. In one embodiment, the pomegranate peel dye is present in an amount of 5 to 15 wt. %, preferably 6 to 14 wt. %, preferably 7 to 13 wt. %, preferably 8 to 12 wt. %, preferably 8 to 11 wt. %, preferably 8 to 10 wt. %, preferably 8 to 9 wt. %, most preferably 8 wt. %.

Figure 2J:
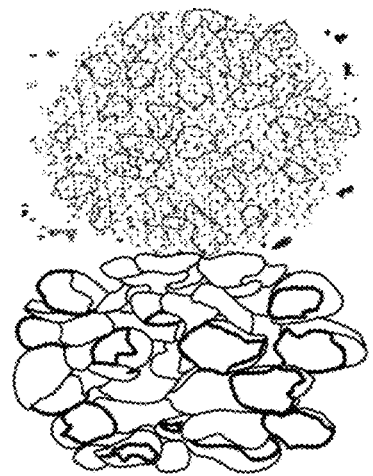
FIG. 2J is a pictorial image of a pomegranate peel, according to certain embodiments.
Figure 2K:
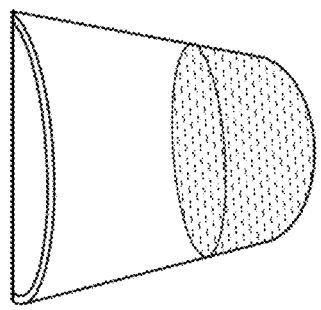
FIG. 2K is a pictorial image of a mangosteen peel and its powder, according to certain embodiments.
Figure 2L:
FIG. 2L is a pictorial image of a colored solution (dye) obtained on the extraction of the pomegranate peel/mangosteen peel, according to certain embodiments.

Pomegranate peels are high in tannin and can be used as a natural dye. When extracted from pomegranate peels, the resulting dye is a green-yellow color of varying intensity. Mangosteen peels contain flavan-3,4-diols, which are classified as tannin compounds and can be used as natural dyes on fabric. When extracted from mangosteen peels, the resulting natural dye obtained is generally a red, a purple, and/or a blue color depending on the extraction method. In some embodiments, the mangosteen peel dye and the pomegranate peel dye are obtained by grinding both the pomegranate peels (FIG. 2J) and mangosteen peels (FIG. 2K) into a fine powder. In one embodiment, the fine powder obtained from the pomegranate peels and the mangosteen peels has an average particle size of 100 to 200 μm, preferably 100 to 200 μm, preferably 100 to 200 μm, preferably 110 to 190 μm, preferably 120 to 180 μm, preferably 130 to 170 μm, preferably 140 to 160 μm, most preferably 150 μm. Once the fine powders of the mangosteen and pomegranate peels are obtained, the pigments are extracted from the peels by simmering the peels in a solvent, the length of simmering depending on the dye shade desired. In one embodiment, the peels are boiled in the solvent for 1 to 24 h, preferably 2 to 22 h, preferably 2 to 20 h, preferably 2 to 18 h, preferably 2 to 16 h, preferably 2 to 14 h, preferably 2 to 12 h, preferably 2 to 10 h, preferably 2 to 8 h, preferably 2 to 6 h, preferably 2 to 4 h, most preferably 2 h. Any suitable solvent may be used such as water, ethanol, acetone, methanol, acetonitrile, dimethyl sulfoxide (DMSO), chloroform, n-hexane, ethyl acetate, toluene, dichloromethane (DCM), isopropanol, or any other suitable extraction solvent. In one embodiment, the extraction solvent is water. In one embodiment, the pigments from the peels of mangosteen and pomegranates are extracted to acquire a similar color to that of the muscles and tissues surrounding the dental crown being prepared (FIG. 2L).

The nanostarch biocomposite thus obtained is in the form of nanoparticles having an average particle size of less than 25 nm, preferably less than 24 nm, preferably less than 23 nm, preferably less than 22 nm, preferably less than 21 nm, preferably less than 20 nm, preferably less than 19 nm, preferably less than 18 nm, preferably less than 17 nm, preferably less than 16 nm, and more preferably less than 15 nm.

Figure 2O:
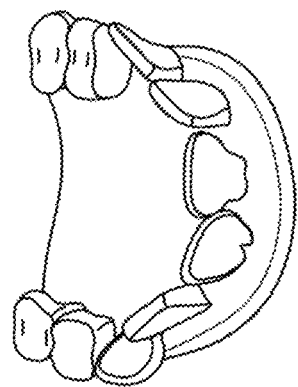
FIG. 2O and FIG. 2P is a pictorial image of organic teeth with color and white, respectively, according to certain embodiments.
Figure 2N:
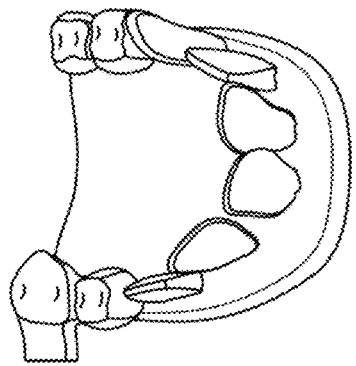
FIG. 2N is a pictorial image of the plasticizer mixture in its final stage, according to certain embodiments.
Figure 2M:
FIG. 2M is a pictorial image of a plasticizer mixture in an initial stage, according to certain embodiments.
Figure 2Q:
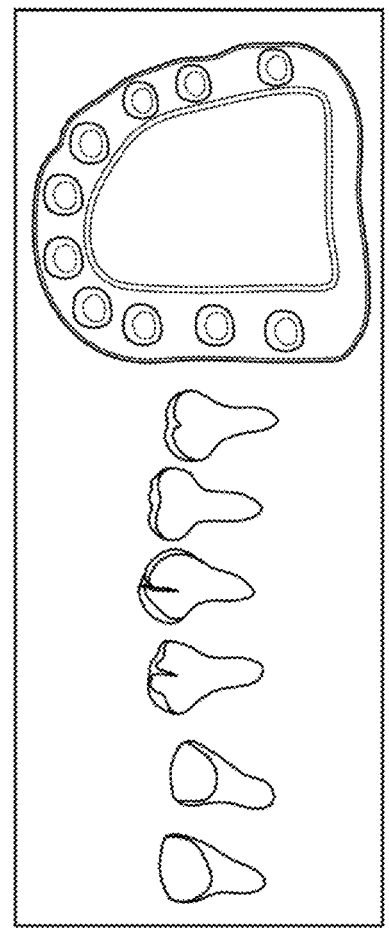
FIG. 2Q is a pictorial image of different organic teeth with color based dyes of present disclosure, according to embodiments.
Figure 2P:
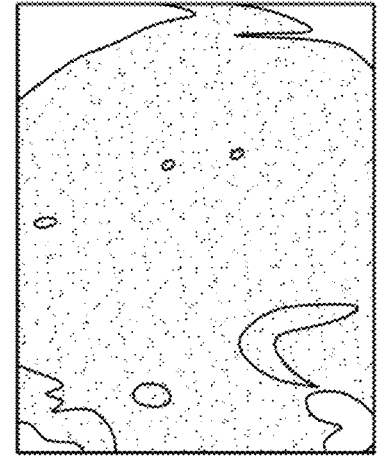

At step 106, the method 100 comprises combining the organic polymer-forming agent with the nanostarch biocomposite to form a dental mixture, then pressing the dental mixture into a molded structure. In one embodiment, the organic polymer-forming agent may be at least one of a polyvinyl chloride (PVC), a polylactic glycolic acid (PLGA), an acrylate adhesive, and a starch, are mixed with the nanostarch biocomposite. In some embodiments, the organic polymer-forming agent comprises at least one of a PVC, an acrylate adhesive, a PLGA, and a starch. In one embodiment, a plasticizer is mixed with the nanostarch biocomposite to form the dental mixture. In one embodiment, the plasticizer is blended with the nanostarch biocomposite in a blender for a period of 5 to 10 min to allow proper mixing of the components (FIG. 2M). In certain embodiments, pyrolysis may be carried out after mixing until the mixture appears plasticized (FIG. 2N) and a dental mixture is obtained. The dental mixture may then be further compressed to form a molded structure. A pictorial image of organic teeth with color and white is depicted in FIG. 2O and FIG. 2P.

Figure 2S:
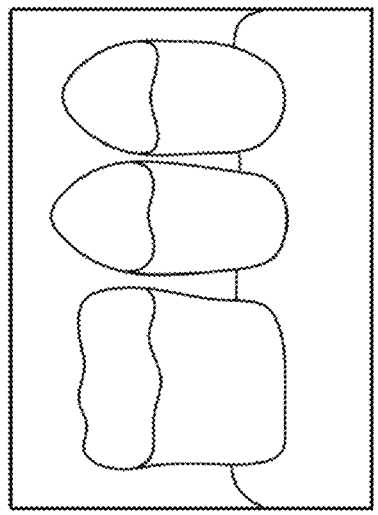
FIG. 2S is a pictorial image of synthetic teeth (plastic), according to certain embodiments.
Figure 2R:
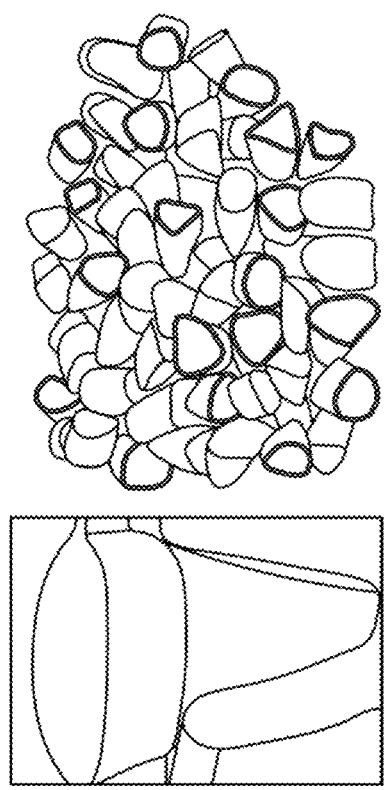
FIG. 2R is a pictorial image of synthetic teeth and cap (plastic and ceramic), according to certain embodiments.

At step 108, the method 100 comprises hardening or curing the molded structure to form the dental crown. The molded structure is further cured via photocuring or thermal curing to form the dental crown. Thermal curing is the process of temperature-induced chemical change in a material, such as the polymerization of a thermoset resin. Photocuring, also known as photopolymerization, is a process that hardens a substance by exposing it to a specific wavelength of light. The process involves irradiating specially formulated compositions, usually liquid and solventless, with ultraviolet or visible light to rapidly convert them into solid films. In an embodiment, the molded structure is cured by photocuring with a light curing device for 10 to 30 seconds(s) at a light intensity of 250 to 850 mW/cm$^2$. In one embodiment, the molded structure is cured with a light curing device for 11 to 29 s, preferably 12 to 28 s, preferably 13 to 27 s, preferably 14 to 26 s, preferably 15 to 25 s, preferably 16 to 24 s, preferably 17 to 23 s, preferably 18 to 22 s, preferably 19 to 20 s. In one embodiment, the molded structure is cured at a light intensity of 250 to 850 mW/cm$^2$, preferably 260 to 840 mW/cm$^2$, preferably 270 to 830 mW/cm$^2$, preferably 280 to 820 mW/cm$^2$, preferably 290 to 810 mW/cm$^2$, preferably 300 to 800 mW/cm$^2$, preferably 310 to 790 mW/cm$^2$, preferably 320 to 780 mW/cm$^2$, preferably 330 to 770 mW/cm$^2$, preferably 340 to 760 mW/cm$^2$, preferably 350 to 750 mW/cm$^2$, preferably 360 to 740 mW/cm$^2$, preferably 370 to 730 mW/cm$^2$, preferably 380 to 720 mW/cm$^2$, preferably 390 to 710 mW/cm$^2$, preferably 400 to 700 mW/cm$^2$, preferably 400 to 690 mW/cm$^2$, preferably 400 to 680 mW/cm$^2$, preferably 400 to 670 mW/cm$^2$, preferably 400 to 660 mW/cm$^2$, preferably 400 to 650 mW/cm$^2$, preferably 400 to 640 mW/cm$^2$, preferably 400 to 630 mW/cm$^2$, preferably 400 to 620 mW/cm$^2$, preferably 400 to 610 mW/cm$^2$, preferably 400 to 600 mW/cm$^2$, preferably 400 to 590 mW/cm$^2$, preferably 400 to 580 mW/cm$^2$, preferably 400 to 570 mW/cm$^2$, preferably 400 to 560 mW/cm$^2$, preferably 400 to 550 mW/cm$^2$, preferably 400 to 540 mW/cm$^2$, preferably 400 to 530 mW/cm$^2$, preferably 400 to 520 mW/cm$^2$, preferably 400 to 510 mW/cm$^2$, most preferably 400 to 500 mW/cm$^2$. In another embodiment, the molded structure is cured by thermal curing at a temperature of 100 to 160° C. for 3 to 6 h. In one embodiment, the molded structure is cured at a temperature of 105 to 155° C., preferably 110 to 150° C., preferably 115 to 145° C., preferably 120 to 140° C., preferably 125 to 135° C., most preferably 130° C. Different organic teeth with color base dice are shown in (FIG. 2Q), and prepared synthetic teeth and caps (plastic and ceramic) are shown in (FIG. 2R and FIG. 2S).

The dental crown of the present disclosure has a tensile strength of 80 to 120 mPa/kg·m³. preferably 85 to 115 kg·m³ preferably 90 to 110 kg·m³, preferably 95 to 100 kg·m³, preferably 98 kg·m³; and a tensile modulus of 1.5 to 2.5 GPa, preferably 1.6 to 2.4 GPa, preferably 1.7 to 2.3 GPa, preferably 1.8 to 2.2 GPa, preferably 1.9 to 2.1 GPa, preferably 1.9 to 2 GPa, most preferably 1.9 GPa.

The visual look of teeth may be characterized by hue (H), lightness (L*), chroma (C), a*, and b*. Hue describes the dominant shade of the tooth (more yellowish or reddish), value is the lightness or darkness of the tooth shade measured independently of the hue, and chroma is the quality that distinguishes the degree of vividness of the hue. Both a* and b* relate to the color coordinates of an object, with a* representing the red-green color coordinate and b* representing the yellow-blue color coordinate. The dental crown formed form the nanostarch biocomposite has a L* of 70 to 90, preferably 71 to 89, preferably 72 to 88, preferably 73 to 87, preferably 74 to 86, preferably 75 to 85, preferably 76 to 84, preferably 77 to 83, preferably 78 to 82, preferably 79 to 82, preferably 80 to 82, preferably 81 to 82, most preferably 81.32. In one embodiment, the dental crown formed form the nanostarch biocomposite has a chroma (C) value of 15 to 30, preferably 16 to 29, preferably 17 to 28, preferably 18 to 27, preferably 19 to 26, preferably 20 to 25, preferably 21 to 24, preferably 21 to 23, preferably 21 to 22, most preferably 21.93. In one embodiment, the dental crown formed form the nanostarch biocomposite has a hue (H) of 85 to 100, preferably 86 to 99, preferably 87 to 98, preferably 86 to 97, preferably 85 to 96, preferably 86 to 95, preferably 87 to 94, preferably 88 to 93, preferably 89 to 93, preferably 90 to 93, preferably 91 to 93, preferably 92 to 93, most preferably 92.56. In one embodiment, the dental crown formed form the nanostarch biocomposite has a a* value of −1 to 0.70, preferably −0.9 to 0.7, preferably −0.8 to 0.7, preferably −0.7 to 0.7, preferably −0.6 to 0.7, preferably −0.5 to 0.7, preferably −0.4 to 0.7, preferably −0.3 to 0.7, preferably −0.2 to 0.7, preferably −0.1 to 0.7, preferably 0 to 0.7, preferably 0.1 to 0.7, preferably 0.2 to 0.7, preferably 0.3 to 0.7, preferably 0.4 to 0.7, preferably 0.5 to 0.7, preferably 0.6 to 0.7, most preferably 0.63. In one embodiment, the dental crown formed form the nanostarch biocomposite has a b* value of 15 to 30, preferably 16 to 29, preferably 17 to 28, preferably 18 to 27, preferably 19 to 26, preferably 20 to 25, preferably 20 to 24, preferably 21 to 23, preferably 21 to 22, most preferably 21.4.

EXAMPLES

The following examples illustrate an organic dental crown. The examples are provided solely for illustration and are not to be construed as limitations of the present disclosure, as many variations thereof are possible without departing from the spirit and scope of the present disclosure.

Example 1: pH and Starch Determination

The pH and cellulose content of the starch of the dental crown of the present disclosure (organic dental crown) were determined, and their values were compared to those of surgical dental crowns available in the market. As used herein, the "organic dental crown" refers to the dental crown derived from biobased sources, of the present disclosure. The quantitative determination of starch was carried out using methods known in the art. The results of this study are depicted in Table 1.

TABLE 1 pH and nanostarch determination

| Materials | pH Determination | Starch Determination |
|---|---|---|
| Organic dental crown | 7.9 ± 0.03 | 50.3% ± 0.01 |
| Synthetic dental crown | Alkaline ≥ 7 | It is zero if from gas or oil, if from starch sample it is 20 to 60%. |

Example 2: Nanostarch Measurement

The particle size of the nanostarch was measured by Scanning Electron Microscopy (SEM), and the results indicate that the nanoparticle size of the organic dental crown was 15 nm in comparison, the nanoparticle size range for standard synthetic dental crowns is typically less than 100 nm. This suggests that the nanostarch biocomposite has a finer particle size, potentially offering unique properties and advantages in dental applications.

TABLE 2

Measurement of nanostarch by SEM

| Materials | Nanostarch size |
|---|---|
| Organic dental crown | 15 nm |
| Synthetic dental crown | 1 to 100 nm (Standard) |

Example 3: Absorption Test (as ASTM D570)

The organic dental crown prepared were further evaluated for their ability to absorb moisture. The tests to determine water absorption were carried out in accordance with ASTM D570. The purpose of ASTM D570 is to determine the rate of water absorption by immersing the specimen (organic dental crown) in water for a specific period of time. In this test, the organic dental crown absorbed 0% water. Water absorption was calculated by determining the percentage increase in weight of the sample following the experiment to characterize this attribute. The results of this study are depicted in Table 3. It can be observed that the water absorption for the organic dental crown prepared by the present disclosure is very low compared to surgical dental crown-suggesting their water-resistant property.

TABLE 3

Determination of water absorption by ASTM D570.

| Materials | Water absorption | ASTM D570 Water absorption |
|---|---|---|
| Organic dental crown | 0% | Water absorption by |
| Synthetic dental crown | 0 to 0.16% | ASTM is 0 to 0.16%. |

Example 4: Burning Test

The organic dental crown was burned using a gas burner. Odor, flame color, speed of burning, and spark were observed visually and compared with the synthetic dental crown by ASTM D3801. Yellow-orange flame, no sparking and burning speed were found the positive effect. The results of this study are depicted in Table 4.

TABLE 4

Burning test according to the ASTM D3801

| Materials | Odor | Color of flame | Speed of burning | Spark or not |
|---|---|---|---|---|
| Organic dental crown | Low odor | Yellow-orange | Slow | Spark |
| Synthetic dental crown | Low odor | Yellow-orange | Slow | Spark |

Example 5: Color Test

Color coating dye was used as the mode of application. It was attached properly to the organic dental crown and dried after 55 minutes, which is less than the maximum of 2 hours, according to ASTM B 117. The results of this study are depicted in Table 5.

TABLE 5

Organic dye was used as the mode of application by ASTM B 117.

| Materials | Color Test (Drying Time) | ASTM B117 |
|---|---|---|
| Organic dental crown | 55 minutes | Maximum 2 hours |
| Synthetic dental crown | 2 hours (maximum) | |

Example 6: Determination of Size and Shape Characteristics by ASTM a 500

The organic dental crown was tested for fracture and shrinkage which shown no increase or decrease in its shape and size after the experiment. There was no change in its shape and size as per ASTM A500. The results of this study are depicted in Table 6.

TABLE 6

Determination of size and shape characteristics of the organic dental crown

| Materials | Size and Shape | ASTM A 500 |
|---|---|---|
| Organic dental crown | No swell or shrink | Resistant Characters |
| Synthetic dental crown | No swell or shrink | |

Example 7: Energy Test

The energy was tested using the following equation: $E=\frac{1}{2}mv^2$ in accordance with ASTM E1886. The results of this study are depicted in Table 6.

TABLE 7

Energy test of the Nanocomposite dental crown (ASTM E1886)

| Materials | Energy ($E = \frac{1}{2} \times M \times V^2$) | ASTM E1886 |
|---|---|---|
| Organic dental crown | 2.5 Joule | |
| Synthetic dental crown | 1.0 to 25 Joule | |

Example 8: Firmness Test

No bore or cracks were observed as per ASTM D2925 or ASTM D5419, respectively. The results of this study are depicted in Table 8.

TABLE 8

Firmness test represented by bore and crack test.

| Materials | Bore test ASTM D2925 | Crack test by ASTM D5419 |
|---|---|---|
| Organic dental crown | No bore symptom | No crack symptom |
| Synthetic dental crown | No bore symptom | No Crack symptom |

Example 9: Tensile Test

The tensile test was done by a Universal Test Machine for bioplastics as ASTM D5083. Results showed the tensile strength was 98 MPa and the tensile modulus was 1.9 GPa for the organic dental crown and were compared with the synthetic dental crown standard given by ASTM D5083. The results of this study are depicted in Table 9.

TABLE 9

Determination of tensile test by using ASTM by ASTM D5083

| Materials | Tensile strength (MPa/kg · m$^3$) | Tensile Modulus (GPa) |
|---|---|---|
| Organic dental crown | 98.0 | 1.9 |
| Synthetic dental crown | 70 to 230 (ASTM) | 1.0 to 3.0 (ASTM) |

Example 10: Melting Point

The hot water (heating) resistance and melting points are adhered to the standard. The odor, hot water heating, and melting point tests were conducted according to ASTM standards.

TABLE 10

Determination of melting point and heating point test by ASTM D5083

| Materials | Melting Point (° C.) | Hot water resistance at 150 (° C.) for 3 h |
|---|---|---|
| Organic dental crown | 200° C. | Color and shape unchanged |
| Synthetic dental crown | 160 to 210° C. | Color and shape unchanged |

Example 11: Chemical Element Test

Chemical element tests, such as Na, K, $CO_3^-$, Cl, Si, Fe, Pb, Cu, Al, Sn, and Zn, were determined using the EN (166) [European Norm, 166] standardization. Compared to the synthetic dental crown, similar results were exhibited. All the elements showed values under the standard. The results of this study are depicted in Table 11.

TABLE 11

Determination of Chemical Element Test
by EN (European Standard EN166))

| Chemical Elements (PPM) | Nanocomposite dental crown | Synthetic dental crown |
|---|---|---|
| K | 9.5 ± 0.4b | 10 |
| Na | 5.5 ± 0.3bc | 5 |
| Cl | 0.59 ± 0.02d | 2 |
| $CO_3^-$ | 145 ± 1.0a | 440-5 |
| Ca | 10.0 ± 0.02a | 10 |
| Si | 3.5 | 5 |
| Fe | 1.9 | 5 |
| Pb | 0 | 5 |
| Cu | 0.4 | 5 |
| Al | 1.5 | 5 |
| Sn | 1.3 | 5 |
| Zn | 0.9 | 5 |

Mean±standard error (SE, n=3). Different letters mean the significant difference at a 5% level of significance by LSD test.

Numerous modifications and variations of the present disclosure are possible in light of the above teachings. It is, therefore, to be understood that within the scope of the appended claims, the invention may be practiced otherwise than as specifically described herein.

The invention claimed is:

1. An organic dental crown, comprising:
   a nanostarch biocomposite comprising an organic composition and a starch biopolymer; and
   at least one organic polymer-forming agent,
   wherein the starch biopolymer comprises date seed-based nanostarch, coconut shell-based nanostarch, fish bone, and camel bone powder,
   wherein the organic composition comprises at least one of a fruit waste, a placenta glue, a seed-based gel, a natural glue, a glycerin, and an organic dye,
   wherein the nanostarch biocomposite comprises particles having an average particle size of less than 25 nm dispersed in a solid matrix, and
   wherein the dental crown has a molded structure having a height of 10 mm or less and a width of 9.5 mm or less.

2. The dental crown of claim 1, wherein the particles of the nanostarch biocomposite have an average particle size of 15 nm or less.

3. The dental crown of claim 1, wherein the organic polymer-forming agent is at least one selected from the group consisting of a plasticizer, an adhesive, a starch, and a glycolic acid copolymer.

4. The dental crown of claim 1, wherein the organic polymer-forming agent comprises polyvinyl chloride.

5. The dental crown of claim 1, wherein the molded structure has an outer layer and a base layer,
   wherein the base layer and the outer layer have a thickness of 1 mm or less.

6. The dental crown of claim 1, having a tensile strength of 80 to 120 mPa/kg·m³.

7. The dental crown of claim 1, wherein the organic dye is at least one selected from the group consisting of a mangosteen peel dye and a pomegranate peel dye.

8. The dental crown of claim 1, having a lightness (L*) of 70 to 90.

9. The dental crown of claim 1, having a chroma (C) value of 15 to 30.

10. The dental crown of claim 1, having a tensile modulus of 1.5 to 2.5 GPa.

11. The dental crown of claim 1, having a hue (H) of 85 to 100.

12. The dental crown of claim 1, having an a* value of −1 to 0.70.

13. The dental crown of claim 1, having a b* value of 15 to 30.

14. A method for fabricating the dental crown of claim 1, comprising:
   hydrolyzing the mixture of the starch biopolymer and the organic composition with at least one inorganic acid to obtain the nanostarch biocomposite;
   combining the organic polymer-forming agent with the nanostarch biocomposite to form a dental mixture, then pressing the dental mixture into a molded structure; and
   hardening or curing the molded structure to form the dental crown.

15. The method of claim 14, wherein the inorganic acid is selected from the group consisting of hydrochloric acid, nitric acid, hydrobromic acid, sulfuric acid, hydrofluoric acid, and phosphorous acid.

16. The method of claim 14, wherein the inorganic acid is sulfuric acid and nitric acid.

17. The method of claim 14, further comprising:
   pyrolyzing the mixture of date seed-based nanostarch, coconut shell-based nanostarch, fish bone, and camel bone powder in an oven at a temperature of 120 to 160° C. for 3 to 8 hours (h).

18. The method of claim 14, wherein the curing is photocuring or thermal curing.

19. The method of claim 14, wherein the molded structure is cured with a photocuring device for 10 to 30 seconds at a light intensity of 250 to 850 mW/cm².

20. The method of claim 14, wherein the molded structure is thermally cured at a temperature of 100 to 160° C. for 3 to 6 h.

* * * * *